United States Patent [19]

Ellis-Davies et al.

[11] Patent Number: 5,446,186
[45] Date of Patent: Aug. 29, 1995

[54] STRUCTURE AND SYNTHESIS OF NITROPHENYL-EGTA, A CAGED CALCIUM, INTERMEDIATES THEREOF AND A METHOD OF PRODUCING A HIGH PHOTOCHEMICAL YIELD OF LIBERATED CALCIUM

[76] Inventors: Graham C. R. Ellis-Davies, 3714 Hamilton St., Philadelphia, Pa. 19104; Jack H. Kaplan, 525 Glenwood Rd., Merion, Pa. 19066

[21] Appl. No.: 149,417

[22] Filed: Nov. 9, 1993

[51] Int. Cl.$^6$ .................. C07F 13/00; C07F 3/00; C07C 229/00
[52] U.S. Cl. ..................... 556/50; 556/131; 556/148; 562/434; 562/489; 562/565; 562/568; 564/441; 564/442; 564/443; 568/44; 568/45; 568/46; 568/54; 568/55; 568/56; 568/584; 568/587; 568/588; 568/593; 568/608; 568/630; 568/651; 568/656; 568/662; 568/663; 204/157.4
[58] Field of Search .................. 556/50, 131, 148; 562/434, 489, 565, 568; 514/492; 564/441, 441, 443; 568/44, 45, 46, 54, 55, 56, 584, 587, 588, 593, 608, 630, 651, 656, 662, 663; 204/157.4

[56] References Cited

U.S. PATENT DOCUMENTS 4,981,985 1/1991 Kaplan et al. .................. 556/50

OTHER PUBLICATIONS

Kaplan, J. H. (1990 *Annu. Rev. Physiol.* 52, 897–914.
Adams, S. R., Kao, J. P. Y., Grynkiewicz, G., Minta, A., & Tsien, R. Y. (1988) *J. Am. Chem. Soc.* 110, 3212–3220.
Ellis–Davies, G. C. R., & Kaplan, J. H. (1988) *J. Org. Chem.* 53, 1966–1969.
Kaplan, J. H., & Ellis–Davies, G. C. R. (1988) *Proc. Natl. Acad. Sci. U.S.A.* 85, 6571–6575.
Morad, M., Davies, N. W., Kaplan, J. H., & Lux, H. D. (1988) *Science* 241, 842–844.
Niggli, E. and Lipp, P. (1993) *Biophys J.* 55 400a.
Naebauer, M., Ellis–Davies, G. C. R., Kaplan, J. H. & Morad, M. (1989) *Am. J. Physiol.* 256, H916–20.
Delaney, K. R., & Zucker, R. S. (1990) *J. Physiol.* 426, 473–498.
Rapp, G., Poole, K. J. V., Maeda, Y., Kaplan, J. H., Ellis–Davies, G. C. R., McCray, J. A., & Goody, R. S. (1990) *Bunseges. Phys. Chem* 93, 410–424.
Iino M, & Endo, M (1992) *Nature* 360, 76–78.

(List continued on next page.)

*Primary Examiner*—Joseé G. Dees
*Assistant Examiner*—Porfirio Nazario-Gonzalez

[57] ABSTRACT

The synthesis and compound of a new caged calcium which is an ortho-nitrophenyl derivative of EGTA and various intermediates. It is synthesized in ten steps and 24% overall yield. The photosensitive chelator, nitrophenyl-EGTA, has a $K_d$ for $Ca^{2+}$ of 80 nM and for $Mg^{2+}$ of 8.8 mM. Upon exposure to ultra-violet light (in the region of 350 nm), the chelator is cleaved, yielding iminodiacetic acid photoproducts with known low Ca-affinity ($K_d$=1 mM). The quantum yield of photolysis of nitrophenyl-EGTA in the presence of $Ca^{a+}$ is 0.23 and in the absence of $Ca^{2+}$ is 0.20. In experiments with chemically skinned skeletal muscle fibers, a fully relaxed fiber equilibrated with nitrophenyl-EGTA:$Ca^{2+}$ complex, in the presence of physiological [$Mg^{2+}$] (i.e. 1.0 mM), produced maximal contraction after a single flash from a frequency doubled ruby laser (347 nm). Half-maximal tension was achieved in 18 ms at 15° C. Nitrophenyl-EGTA provides a new tool for the investigation of the mechanism of $Ca^{2+}$-dependent physiological processes, since under conditions of normal intracellular $Ca^{2+}$ and $Mg^{2+}$ ions, only $Ca^{2+}$ ions are bound by the photolabile chelator and on illumination are released rapidly and in high photochemical yield.

11 Claims, 10 Drawing Sheets

OTHER PUBLICATIONS

Allen, T. S., Barsotii, R. J., Ellis–Davies, G. C. R., Kaplan, J. H. Goldman, Y. E., Martyn, D. A., & Gordon, A. M. (1993) *Biophys. J.* 64, 135a.

Neher, E. & Zucker, R. S. (1993) *Neuron* 10, 21–30.

Thomas, P., Wong, J. G., & Almers, W. *EMBO J.* 12, 303–306. (1993).

Johnson, B. D. & Byerly, L. (1993) *J. Physiol.* 462, 321–347.

Zucker, R. S. (1992) *Cell Calcium* 13, 29–40.

Kaplan, J. H., Forbush, B., & Hoffman, J. F. (1978) *Biochemistry* 17, 1929–1935.

Minta, A., Kao, J. P. Y., & Tisen, R. Y. (1989) *J. Biol. Chem.* 264, 8171–8178.

McCray, J. A., Fidler–Lim, N., Ellis–Davies, G. C. R., & Kaplan, J. H. (1992) *Biochemistry* 31, 8856–8861.

Zucker, R. S. (1993) *Cell Calcium* 14, 87–100.

Harkins, A. B., Kurebayashi, N., & Baylor, S. M. (1993) *Biophys. J.* 64, 241a.

Konishi, M. & Baylor, S. M. (1991) *J. Gen Physiol.* 97, 245–270.

Pape, P. C., Konishi, M., Hollingworth, S., & Baylor, S. M. (1990) *J. Gen. Phys.* 96, 493–516.

Goldman, Y. G., Hibberd, M. G., & Trentham, D. R. (1984) *J. Physiol.* 354, 701–705.

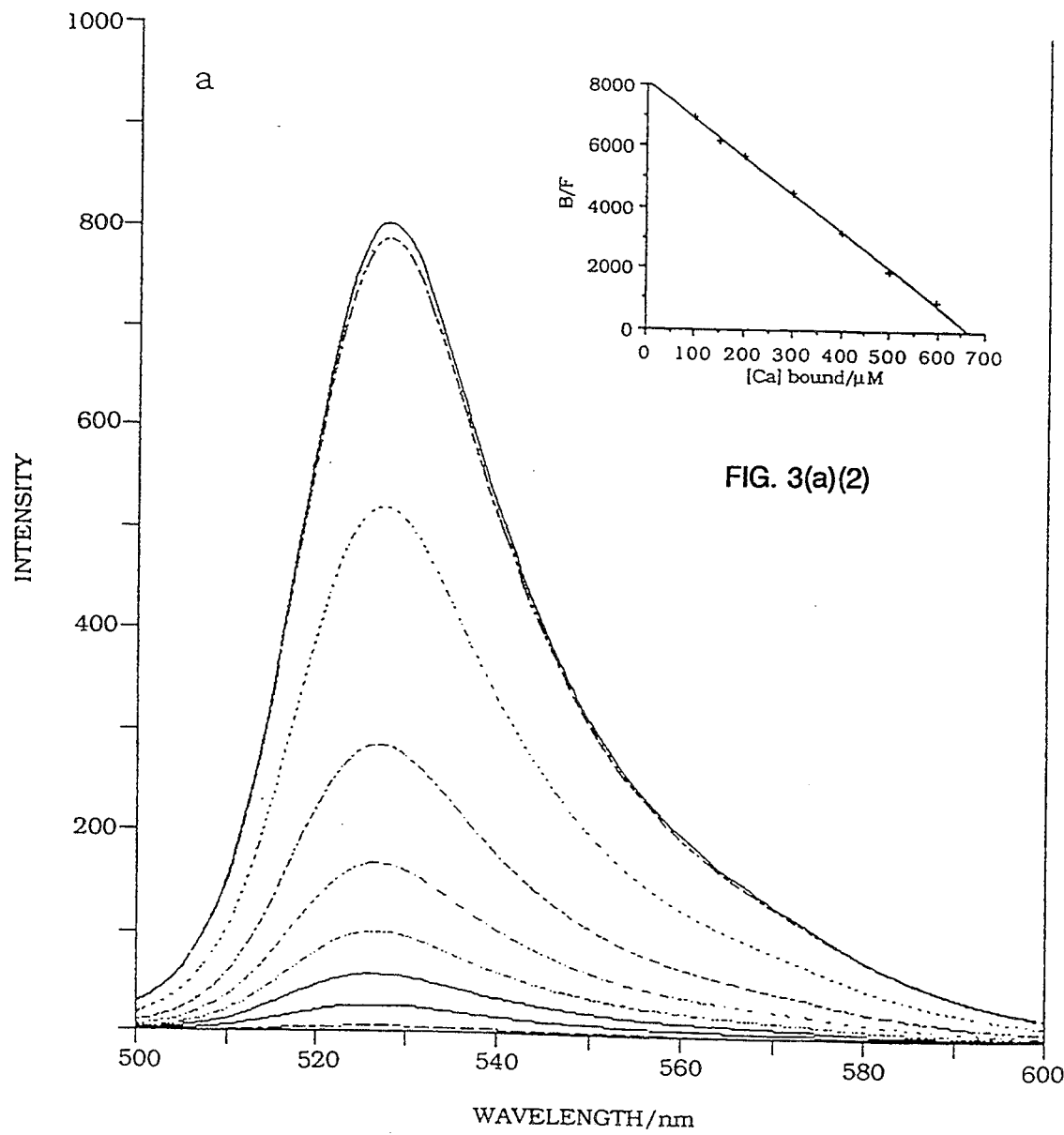
FIG. 3(a)(2)
FIG. 3(a)(1)

SCHEME 3

$R_1$-$R_4$ = hydrogen, methoxy, halogen, methyl, hydroxy, vinyl, nitro, amino, thioalkyl or dimethylamino $R_5$ and/or $R_6$ = hydrogen, methyl or ethyl

STRUCTURE AND SYNTHESIS OF NITROPHENYL-EGTA, A CAGED CALCIUM, INTERMEDIATES THEREOF AND A METHOD OF PRODUCING A HIGH PHOTOCHEMICAL YIELD OF LIBERATED CALCIUM

BACKGROUND OF THE INVENTION

Abbreviations

TFA, trifluoroacetic acid
Hepes, N-2-hydroxyethylpiperazine-N'-2-ethanesulfonic acid
Dibal, diisobutyl aluminum hydride
NBS, N-bromosuccinimide
HPLC, high-performance liquid chromatography
Caged $P_i$, 1-(o-nitrophenyl)-ethyl phosphate
BAPTA, 1,2-bis(o-aminophenoxy)ethane-N,N,N',N'-tetraacetic acid
EDTA, ethylenediaminetetraacetic acid
EGTA, ethylenebis(oxyethylenenitrilo)tetraacetic acid
Tes, (N-tris[hyroxymethyl]methyl-2-aminoethanesulfonic acid
HDTA, N-hyroxyethylethylenediaminetriacefic acid Calcium is an important second messenger for a wide variety of physiological and biochemical processes such as muscle contraction, neurotransmitter release, ion channel gating, exocytosis, etc. The essential role of $Ca^{2+}$ release and sequestration in intracellular communication has also been recently highlighted by the growing appreciation of the importance of inositol phospholipid metabolism in signaling. A technique for the controlled, localized, and rapid increase in $[Ca^{2+}]$ would provide a tool which would enable the study of the kinetic, regulatory, and structural mechanisms of such processes to be undertaken. Two approaches to this problem have been taken (reviewed in ref. 1 ). The first, developed by Tsien and co-workers, involves reducing the $Ca^{2+}$-buffering capacity of a BAPTA derivative by decreasing the electron donating capacity of one of the coordinating ligands on illumination following the photoexpulsion of a small molecule from the chelator. This strategy has led to two readily available photosensitive buffers, nitr-5 and nitr-7 (2).

Our approach is conceptually different in that we have designed photosensitive derivatives of chelators with known high affinity for $Ca^{2+}$, which upon illumination are bifurcated, producing two moieties with known low affinity, thus the bound $Ca^{2+}$ is released (cf. Scheme 1).

DM-nitrophen is a (now) commercially available photosensitive derivative of EDTA (3,4) representative of this approach which has found wide application during the last several years as a caged Ca (5-14) and caged Mg (15). The distinct advantage of nitr-5 and nitr-7 compared to DM-nitrophen is that they are $Ca^{2+}$-selective chelators whereas DM-nitrophen has chelation properties similar to EDTA from which it is derived. The comparative advantages of DM-nitrophen are that its $Ca^{2+}$ affinity is very high before photolysis and very low after photolysis, thus ensuring a good photochemical yield of liberated $Ca^{2+}$.

In our U.S. Pat. No. 4,981,985, the entire disclosure of which is incorporated by reference herein, we disclosed the synthesis of photolabile chelators for multivalent cations. The disclosure included the method of synthesizing photolabile chelators as EDTA and EGTA derivatives to be used in caging multivalent cations. The chelators chelate the cations forming non-biologically active compounds. Upon irradiation, the chelated compound cleaves with the subsequent cleaved remainders having a substantially lower affinity for the chelated cation. Large mounts of cation are thus rapidly released and the effect of such concentration jumps on the biological system can be accurately studied.

We now describe a new photosensitive $Ca^{2+}$ chelator, called nitrophenyl-EGTA or NP-EGTA (1), that binds $Ca^{2+}$ selectively with high affinity (80 nM), which upon photolysis is bifurcated producing iminodiacetic acid photoproducts (see Scheme 1 ) with a 12,500-fold lower affinity for $Ca^{2+}$. This new compound possesses the desired properties of $Ca^{2+}$ selectivity in combination with a rapid high photochemical yield of liberated $Ca^{2+}$.

Accordingly, a need exists for a caged calcium which selectively binds $Ca^{2+}$ with high affinity and releases it rapidly upon photolysis.

OBJECTS OF THE INVENTION

Accordingly, it is a general object of this invention to provide a caged calcium which selectively binds $Ca^{2+}$ with high affinity and releases it rapidly upon photolysis.

It is a further object of this invention to provide a synthesis for a caged calcium which selectively binds $Ca^{2+}$ with high affinity and releases it rapidly upon photolysis.

It is another object of this invention to provide a synthesis for a caged calcium which selectively binds $Ca^{2+}$ with high affinity and releases it rapidly upon photolysis which is reproducible and provides a good yield of product.

It is yet another object of this invention to provide a method of producing a high photochemical yield of liberated calcium in a localized area in a controlled manner.

SUMMARY OF THE INVENTION

These and other objects of this invention are achieved by providing a compound of the formula ortho-nitrophenyl-ethylenebis(oxyethylenenitrilo)tetraacetic acid. The invention further includes a method of synthesizing 4-(2'-nitrophenyl)-3,13-bis[carboxymethyl]-6,9-dioxa-3,12-diazatetradecanedioic acid. The invention further includes a method of producing a high photochemical yield of liberated calcium in a localized area in a controlled manner, comprising the steps of binding calcium ions with 4-(2'-nitrophenyl)-3,13-bis[carboxymethyl]-6,9-dioxa-3,12-diazatetradecanedioic acid, introducing the resultant product to a localized area in which the liberated calcium is to be produced and subjecting the product to photolysis. The invention also includes various intermediates prepared in the synthesis.

DESCRIPTION OF THE DRAWINGS

Other objects and many attendant features of this invention will become readily appreciated as the same becomes better understood by reference to the following detailed description when considered in connection with the accompanying drawings wherein:

FIG. 2 shows the quantum yield of nitrophenyl-EGTA photolysis. The filtered output of 1000-W high pressure Hg arc lamp was used to photolyze solutions of NP-EGTA (1.77 mM) or caged-Pi (3.12 mM) in buffer (40 mM hepes, 100 mM KCl, pH 7.2) with absorbances of 0.0105 in a cuvette with a pathlength of 1.0 min. Each solution also contained inosine (100 mM) as the internal standard.

The Table shows the [$Ca^{2+}$]$_{free}$ before (B) and after (A) photolysis at three different ratios of chelator: $Ca^{2+}_{total}$ for nitrophenyl-EGTA, DM-nitrophen, nitr-5 and nitr-7. The change in [$Ca^{2+}$]$_{free}$ is shown as DCa assuming 50% photolysis of the chelator. $K_d$'s and [Ca] are given for pH 7.2 and 100–150 mM ionic strength. (a) EGTA Mg affinity.

Figure 5:
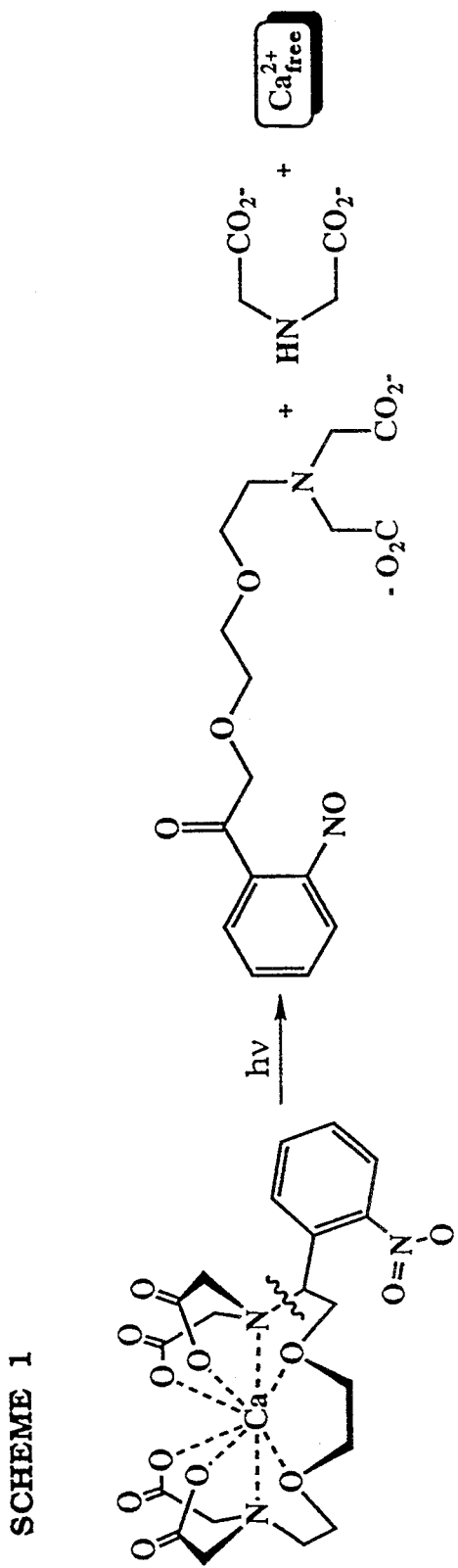

FIG. 5 shows the Photorelease of $Ca^{2+}$ from Nitrophenyl-EGTA.

Figure 6:
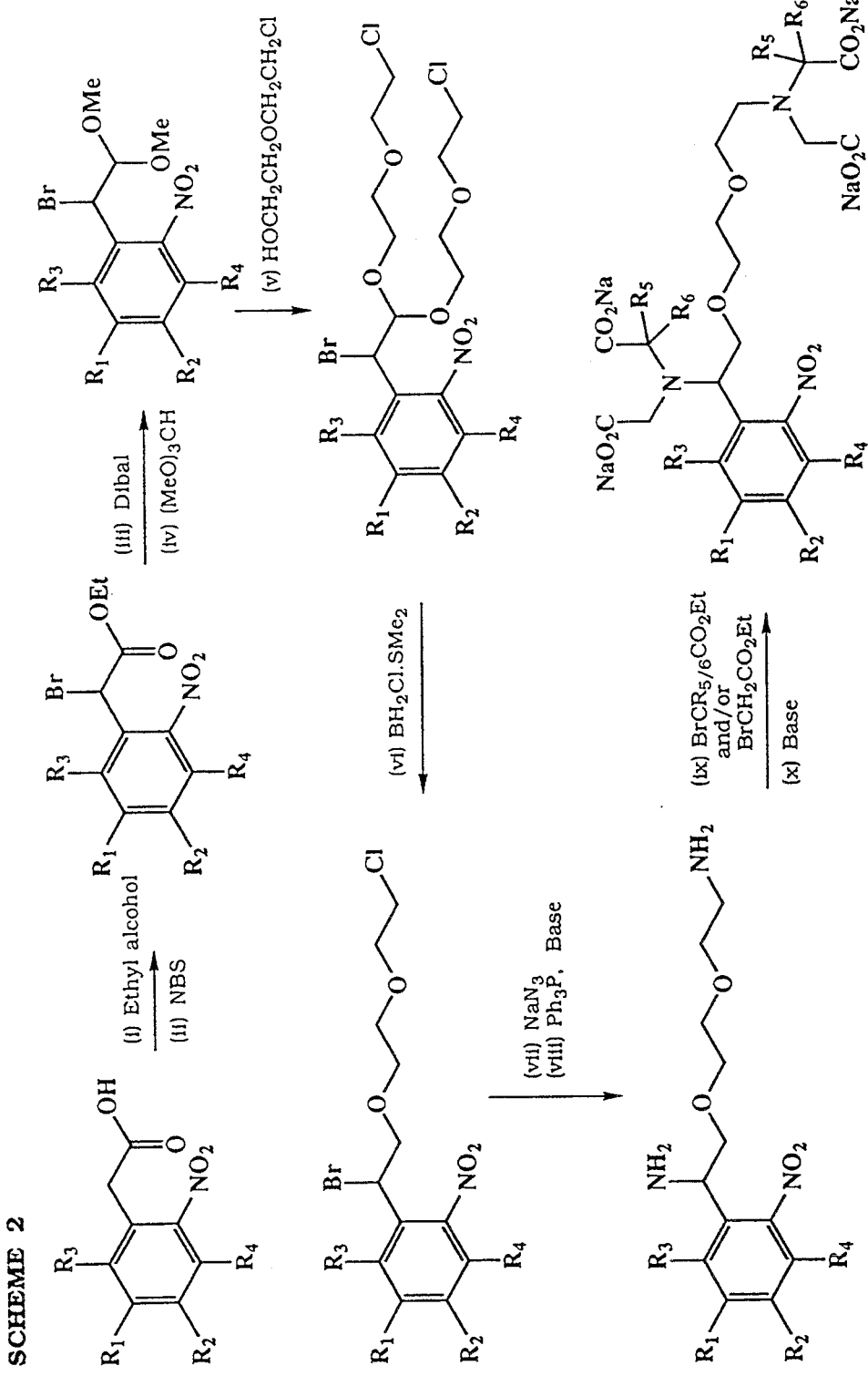

FIG. 6 shows the synthesis of Nitrophenyl-EGTA.

Figure 7:
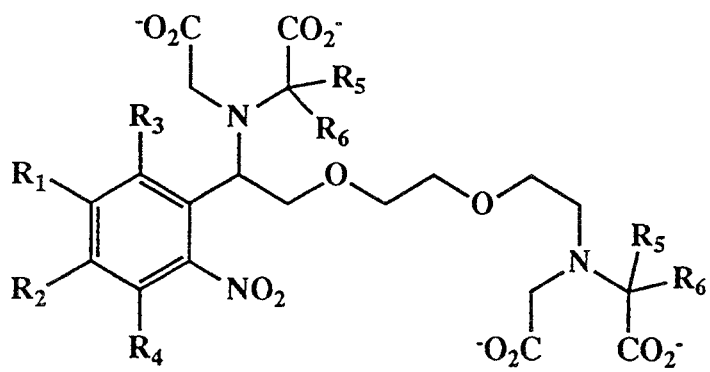

FIG. 7 shows a generalized structure of Nitrophenyl-EGTA with substituents.

DETAILED DESCRIPTION OF THE PREFERRED EMBODIMENTS

The present invention includes the synthesis and properties of a new caged calcium. The compound is an ortho-nitrophenyl derivative of EGTA. It is synthesized in ten steps and 24% overall yield. The photosensitive chelator, nitrophenyl-EGTA, has a $K_d$ for $Ca^{2+}$ of 80 nM and for $Mg^{2+}$ in the mM range. Upon exposure to ultra-violet light (in the region of 350 nm), the chelator is cleaved, yielding iminodiacetic acid photoproducts with known low Ca-affinity ($K_d$=1 mM). The quantum yield of photolysis of nitrophenyl-EGTA in the presence of $Ca^{2+}$ is 0.23 and in the absence of $Ca^{2+}$ is 0.20. In experiments with chemically skinned skeletal muscle fibers, a fully relaxed fiber equilibrated with nitrophenyl-EGTA:$Ca^{2+}$ complex, in the presence of physiological [$Mg^{2+}$] (i.e. 1.0 mM), produced maximal contraction after a single flash from a frequency doubled ruby laser (347 nm). Half-maximal tension was achieved in 18 ms at 15° C. Nitrophenyl-EGTA provides a new tool for the investigation of the mechanism of $Ca^{2+}$-dependent physiological processes, since under conditions of normal intracellular $Ca^{2+}$ and $Mg^{2+}$ ions, only $Ca^{2+}$ ions are bound by the photolabile chelator and on illumination are released rapidly and in high photochemical yield. Other multivalent cations suitable for use in the present invention include zinc, cadmium, manganese and iron.

RESULTS AND DISCUSSION

Synthesis of NP-EGTA

NP-EGTA was synthesized in ten synthetic steps and 24% overall yield as outlined in Scheme 2:

o-Nitrophenylbromoacetic acid, Ethyl Ester (2)

A solution of o-nitrophenylacetic acid (19.0 g, 105 retool), and ethanol (46.0 g, 1 mol) with p-toluenesulphonic acid catalyst in benzene (150 ml) was heated at reflux for 8 h, and water was removed from the reaction mixture by azeotropic distillation. The solution was extracted with a $Na_2CO_3$ solution (100 ml), and the organic phase was concentrated in vacuo to give 19.8 g (95%, 100% based on recovered starting material) of nitroester as a yellow solid, mp 64°–66° C., $R_f$=0.25. A mixture of nitroester (2.0 g, 9.56 mmol) and NBS (1.98, 11.0 mmol) with benzoyl peroxide catalyst in carbon tetrachloride (50 ml) was heated at reflux for 48 h. The mixture was filtered and concentrated in vacuo. Flash chromatography purification (elution with 20% ethyl acetate in hexane) gave 2.48 g (90%) of (2) as a yellow liquid: $^1$H NMR (250 MHz, $CDCl_3$) d 8.20 (ddd, J=8.9, 8.1, 1.8 Hz, 2H), 7.70 (td, J=8.1, 1.8 Hz, 1H), 7.53 (td, J=8.9, 1.8 Hz, 1H), 6.07 (s 1H), 4.29 (q, J=7.1 Hz, 2H), 1.34 (t=J=7.1 Hz, 3H). $R_f$=0.36. (All $R_f$'s are given for the solvent system used for purification.)

o-Nitrophenylbromoacetaldehyde Dimethyl Acetal (3)

To a solution of 2 (3.0 g, 10.4 mmol) in dichloromethane (130 ml) at −78° C. was added Dibal (10.7 mmol from a 1 M solution in hexanes) dropwise over 25 min. The reaction mixture was stirred a further 10 min and then poured into a concentrated sodium tartrate solution (100 ml). This mixture was stirred at room temperature overnight. The organic layer was separated and dried. Montmorillonite clay K-10 impregnated with trimethylorthoformate (9.0 g) was added and the reaction stirred for 1 h. The clay was removed by filtration through Celite and the solution concentrated in vacuo and purified by flash chromatography (elution with 25% ethyl acetate in hexane). The combined yield from two such reactions was 5.83 g (95%) of 3 as a yellow oil: $^1$H NMR (250 MHz, CDCl$_3$) d 7.93 (dd, J=8.0, 1.5 Hz, 1H), 7.83 (dd, J=8.0, 1.5 Hz, 1H), 7.62 (dt, J=8.0, 1.5 H, 1H), 7.44 (dt,J=8.0, 1.5 Hz, 1H), 5.54 (d, J=5.5 H, 1H), 4.67 (d, J=5.5 Hz, 1H), 3.45 (s, 3H), 3.35 (s, 3H). R$_f$=0.31 o-Nitrophenylbromoacetaldehyde Bis-2-(2-chloroethoxy)-ethyl Acetal (4)

A solution of 3 (1.52 g, 5.20 mmol) and 2-(2-chloroethoxy)-ethanol (S.18 g, 41.6 mmol) in anisole (20 ml) with pyridinium p-toluenesulphonate catalyst was heated at 110.171° C. for 7h. The solution was concentrated in vacuo and purified by flash chromatography (elution with 25% ethyl acetate in hexane) to give 1.96 g (79%) of 4 as a yellow oil: $^{1H\,NMR}$ (250 MHz, CDCl$_3$) d 7.94 (dd, J=8.0, 1.4 H, 1H), 7.80 (dd, J=8.0, 1.4 Hz, 1H), 7.60 (td, J=8.0, 1.4 Hz, 1H), 7.43 (td, J=8.0, 1.4 Hz, 1H), 5.87 (d, J=5.5 Hz, 1H), 4.99 (d, J=5.5 Hz, 1H), 3.91–3.50 (m, 16 H). R$_f$=0.24.

2-(2-Chloroethoxy)-ethyl 2-o-Nitrophenyl-2-bromoethyl Ether (5)

A solution of 4 (2.59 g, 5.45 mmol) and monochloroborane-methyl sulphide (2.41 g, 21.8 mmol) in diethyl ether (30 ml) was heated at reflux for 24 h. Water was added, the reaction mixture heated for 5 min and then extracted with dichloromethane. The organic phase was dried, concentrated in vacuo and subjected to flash chromatography on silica gel (elution with 25% ethyl acetate in hexane) to give 1.60 g (84%) of 5 as a yellow oil: $^1$H NMR (250 MHz, CDCl$_3$) d 7.85(dd, J=8.1, 1.3 Hz, 2H), 7.63 (td, J=8.1, 1.3 Hz, 1H), 7.45 (td, J=8.1, 1.3 Hz 1H), 5.82 (t, J=6.7 Hz, 1H), 4.04 (d, J=6.7 Hz, 1H), 3.76–3.56 (m, 8H). IR (CHCl$_3$, cm$^{-1}$) 3020, 2970, 2910, 2880, 1530, 1355, 1120. High resolution mass spectrum, C$_{12}$H$_{15}$ ClBr NO$_4$ requires 350.9873, M+NH$_4^+$ observed 369.0217. Major fragments: 272 (23%) and 274 (8%), ArNO$_2$CHCH$_2$O(CH$_2$)$_2$O(CH$_2$)$_2$Cl; 228 (96%) and 230 (95%), ArNO$_2$CHBrCH$_2$; 137 (100%) and 139 (33%), CH$_2$O(CH$_2$)$_2$ O(CH$_2$)$_2$ Cl; 107 (100%) and 109 (33%), (CH$_2$)$_2$ O(CH$_2$)$_2$ Cl. R$_f$=0.39.

2-(2-Azaethoxy)-ethyl 2-o-Nitrophenyl-2-azaethyl Ether

A solution of 5 (0.309 g), 0.876 mmol) in dimethylformamide (10 ml) was heated at 110° C. with sodium azide (0.171 g, 2.64 mmol) for 5 h. Water was added and the product was extracted into ether. The organic phase was dried, concentrated in vacuo and subjected to flash chromatography on silica gel (elution with 25% ethyl acetate in hexane) to give 0.275 g (99%) of the diazide as a yellow oil: $^1$H NMR (250 MHz, CDCl$_3$) d 7,97 (dd, J=8.0, 1.0 Hz, 1 H) 7.72–7.62 (m, 2H) 7.48 (m, 1H) 5.51 (dd, J=8.0, 4.7 Hz, 1H) 3.86 (dd, J=9.5, 3.7 Hz, 1H) 3.79–3.65 (m, 7H) 3.38 (t, J=4.8 Hz, 2H). IR (CHCl$_3$, cm$^{-1}$) 3010, 2930, 2880, 2105, 1530, 1355, 1290, 1255, 1125. R$_f$=0.39.

2-(2-Aminoethoxy)-ethyl 2-o-Nitrophenyl-2-amino Ether (6)

A solution of the diazide (2.41 g, 7.61 mmol) and triphenylphosphine (12.0 g, 45.7 mmol) in tetrahydrofuran was heated at reflux for 1.5 h. 2N NaOH (40 ml) was added and the reaction mixture was heated for 1.5 h. On cooling IN HCl (100 ml) was added and the reaction mixture extracted with dichloromethane. The pH of the aqueous phase was adjusted to 12 with NaOH(solid) and then extracted with dichloromethane. This organic phase was dried, concentrated in vacuo and purified by flash chromatography on silica gel (elution with MeOH/CH$_2$Cl$_2$/Et$_3$N, 5:4:1) to give 1.54 g (75%) of 6 as viscous yellow oil: $^1$H NMR (250 MHz, CDCl$_3$) d 7.86 (dd, J=8.0, 1.0 Hz, 1H) 7.77 (dd, J=8.0, 1.4 Hz, 1H) 7.59 (dt, J=7.8, 1.4 Hz, 1H) 7.36 (dt, J=8.2, 1.4 Hz, 1H) 4.68 (dd, J=8.0, 3.7 Hz, 1H) 3.73–3.52 (m, 8H) 2.99 (t, J=5.2 Hz, 2H). IR (CHCl$_3$, cm$^{-1}$) 3380, 3300, 2960, 1530, 1360. R$_f$=0.43.

4-(2-Nitrophenyl) -3,13-bis[(ethoxycarbonyl)methyl]-6,9-dioxa-3, 12-diazatetradecanedioic Acid Diethyl Ester A solution of 6 (1.54 g, 5.72 mmol), ethyl bromoacetate (9.52 g, 57.0 mmol), NaI (8.55 g, 57.0 mmol) and 1,2,2,6,6-pentamethylpiperidine (4.44 g, 28.6 mmol) in acetonitrile (60 ml) was heated at reflux for 14 h. Flash chromatographic purification on silica gel (elution with 50% ethyl acetate in hexane) gave 2.29 g (65%) of NP-EGTA, tetraethyl ester as a yellow oil: $^1$H NMR (250 MHz, CDCl$_3$) d 7.97 (dd, J=8.0, 1.5 Hz, 1H) 7.74 (dd, J=8.0, 1.4 Hz, 1H) 7.55 (dt, J=8.5, 1.4 Hz, 1H) 7.37 (dt, J=8.5, 1.4 Hz, 1H) 4.91 (dd, J=6.6, 3.4 Hz, 1H) 4.21–4.06 (m, 8H) 3.80 (dd, J=11.2, 6.6 Hz, 1H) 3.71–3.56 (m,7H) 2.91 (t, J=5.6 Hz, 2H) 1.29–1.19 (m, 12H). $^{13}$C NMR (62,9 MHz, CDCl$_3$) d 171.4, 171.2, 150.0, 135.5, 132.5, 130.4, 123.8, 73.0, 70.2, 70.1, 69.9, 58.9, 55.7, 53.5, 52.8,14.1. IR (CHCl$_3$, cm$^{-1}$) 3040, 2990, 2950, 2910, 2880, 1740, 1530, 1375, 1355, 1200. UV (EtOH) $\epsilon_{250}$=4.14×10$^3$ M$^{-1}$ cm$^{-1}$. High resolution mass spectrum, C$_{28}$H$_{43}$N$_3$ O$_{12}$ requires 613.2847; M+H$^+$ 614.2902 observed. R$_f$=0.13.

4-(2'-Nitrophenyl)-3, 13-bis(carboxymethyl)-6,9,dioxa-3, 12 -diazatetmdecanedioic add, tetra sodium salt (1)

A solution of NP-EGTA, tetraethyl ester (0.599 g, 0.971 mmol) and NaOH (4.4 mmol) in 50% aqueous ethanol was heated at 60° C. for 18 h. Complete hydrolysis of the tetraester to give NP-EGTA, 1, was effected as shown by $^1$H NMR (250 Hz, D$_2$O) d 7.86 (t, J=6.8 Hz, 2H) 7,72 (t, J=7,4 Hz, 1H) 7,$3 (t, J=7.9 Hz, 1H) 4.95 (t, J=6.0 Hz) 4.00 (dd, J=9.0, 4.5 Hz, 1H) 3.83 (dd, J=10.4, 4.2 Hz, 1H) 3.77–3.59 (m, 4H) 3.47 (t J=5.7 Hz, 2H) 3.32–3.08 (m, 8H) 2.68 (t, J=5.7 Hz, 2H).

Spectral Properties

Figure 1:
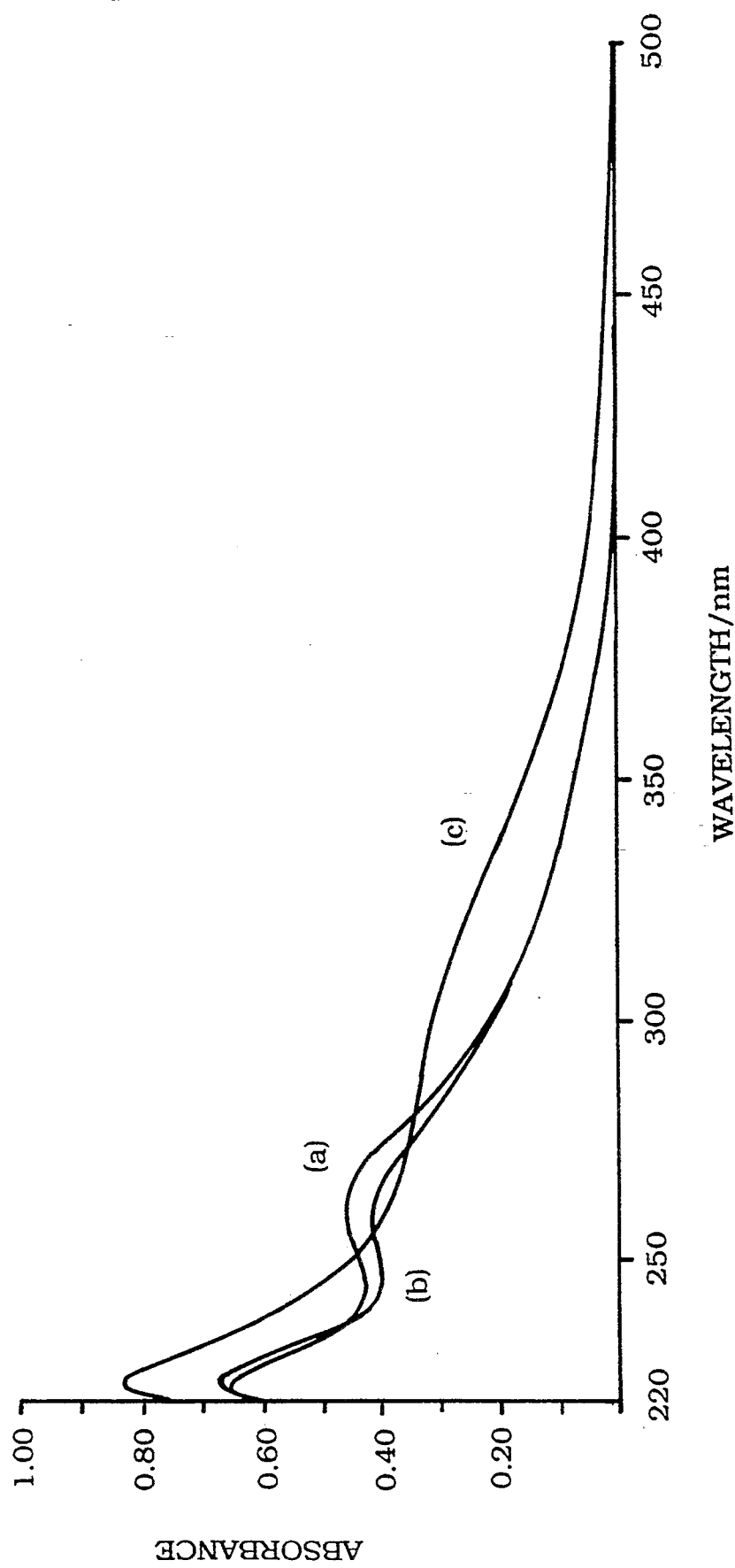
FIG. 1 is an absorption spectra of nitrophenyl-EGTA. The absorption spectrum of a solution of NP-EGTA (66.5 mM) in buffer (40 mM hepes, 100 mM KCl, pH 7.2) is shown (spectrum a). The spectrum is altered (spectrum b) on addition of saturating $Ca^{2+}$ (0.20 mM). Photolysis of this sample for 300 s with the filtered output of a 1-kW Hg arc lamp yielded photoproducts with spectrum (c).

The absorption spectra of NP-EGTA without and with saturating Ca$^{2+}$ are shown in FIG. 1(a) and (b) respectively. The extinction coefficients at 260 and 347 nm are 5.52×10$^3$ M$^{-1}$cm$^{-1}$ and 974 M$^{-1}$ cm$^{-1}$ respectively in Ca$^{2+}$-free buffer (40 mM hepes, 100 mM KCl, pH 7.2). Saturating Ca$^{2+}$ produces a 10% decrease in the absorption at 260 nm. The absorption spectrum changes to that shown in FIG. 1(c) upon complete photolysis in the presence of Ca$^{2+}$. Fluorescence emission spectra of NP-EGTA show that this probe is virtually non-fluorescent (data not shown), as has been reported for DM-nitrophen (16). In fact, fluo-3 saturated with Ca$^{2+}$ is about 2.1×10s-fold more fluorescent at 530 nm than NP-EGTA is at 400 nm.

Quantum Yield

Figure 2A:
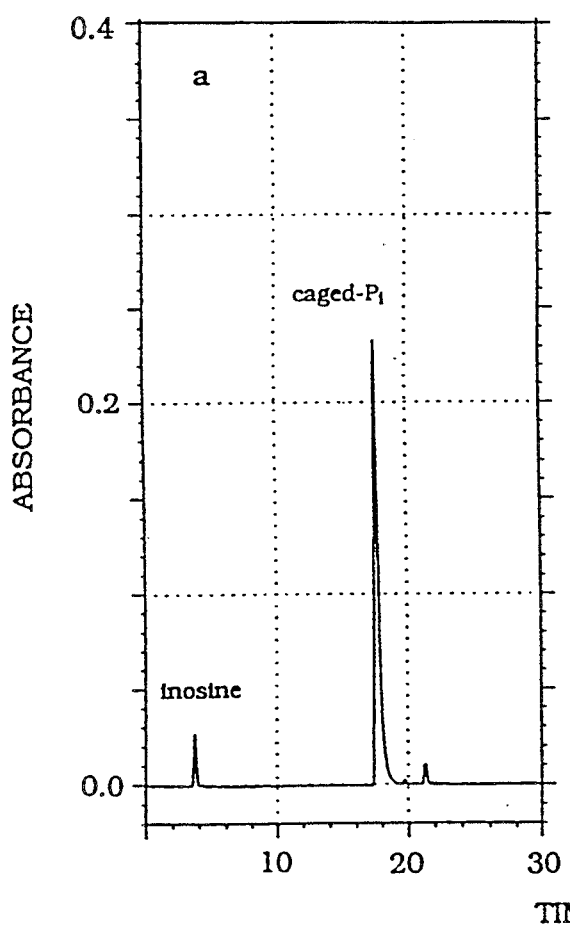
FIG. 2(a) shows the HPLC analysis of photolysis of caged-$P_i$. On the left, t=0 s, on the fight, t=15 s.
Figure 2A:
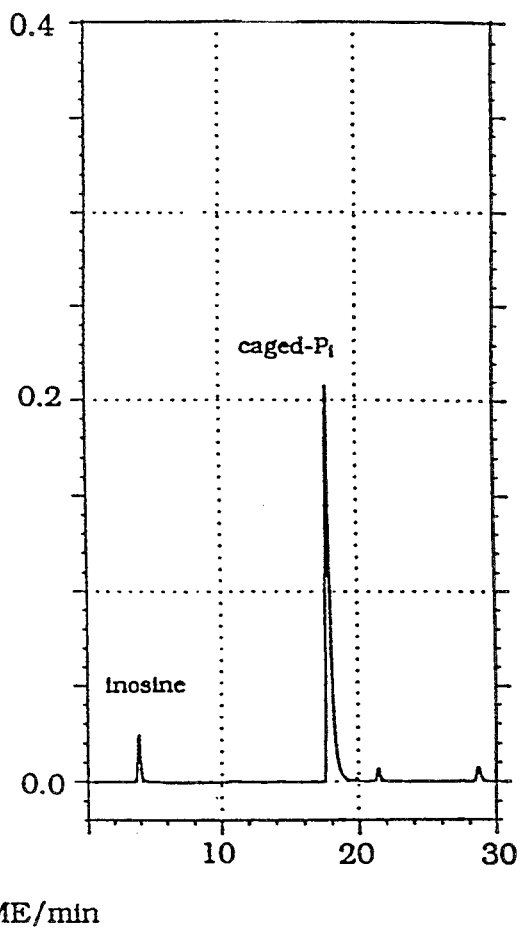
Figure 2B:
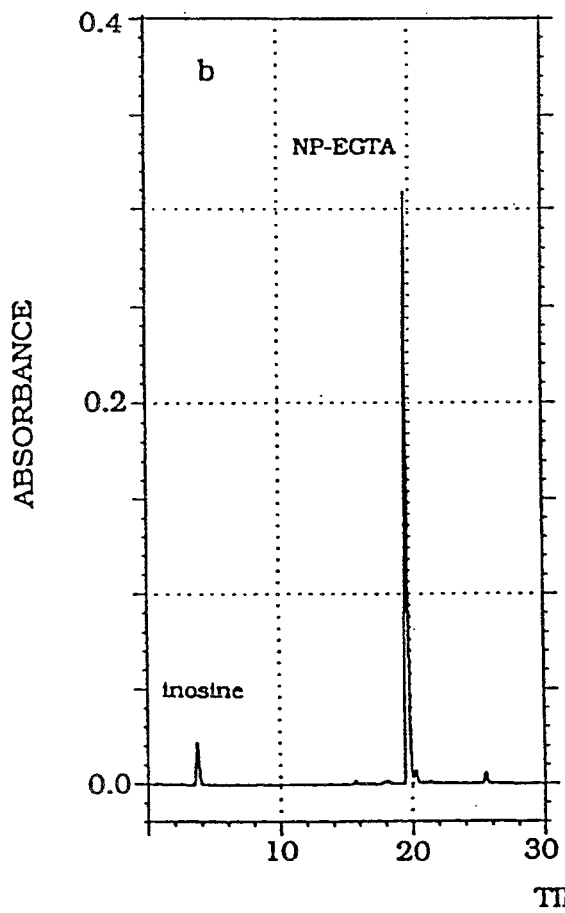
FIG. 2(b) shows the HPLC analysis of the photolysis of the NP-EGTA:$Ca^{2+}$ complex. On the left, t=0 s, on the fight, t=15 s. HPLC was performed using a Novapak $C_{18}$ reverse-phase HPLC column and two Waters 501 pumps fitted with a Waters 680 automated control module delivering 2 ml/min. Pump A delivered 100% $H_2O$/2.5% TFA and pump B 80% acetonitrile/0.052% TFA. The gradient was for 0-5 min 100% A, from 5-20 min a linear change to 80% A, and from 20-40 min 80% A. The eluent was monitored by a Waters 990 photodiode array detector and chromatograms are shown at 260 nm.
Figure 2B:
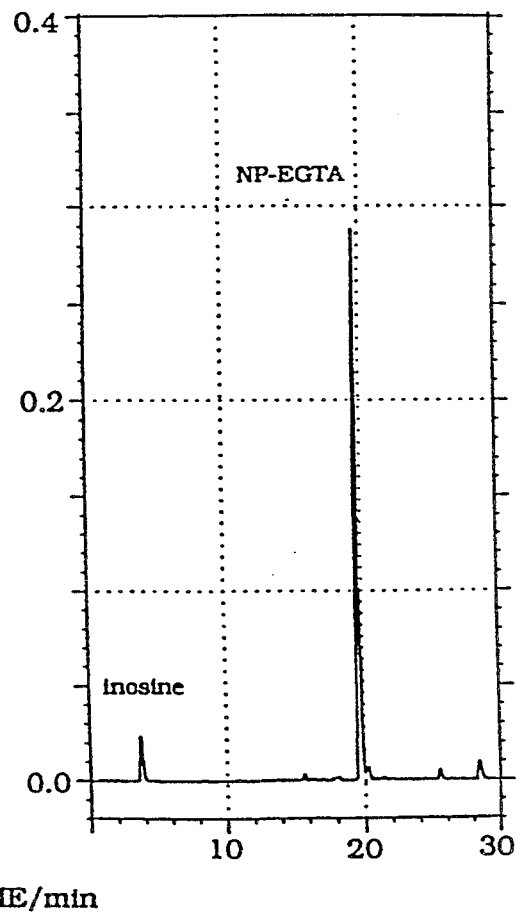

The quantum yield of NP-EGTA photolysis was determined by comparison to that of caged-$P_i$ which has previously been determined to have a quantum yield of photolysis of 0.54 (17). The time-course of disappearance of the caged compounds was followed by HPLC analysis of the reaction mixture (FIG. 2). The amount of NP-EGTA or caged-$P_i$ remaining in the reaction mixture was normalized for each HPLC analysis by comparison to a photochemically inert internal standard, inosine (100 mM). HPLC analysis indicated that after 15 s, 15.1% of the caged-$P_i$ had been photolyzed (FIG. 2a). Under the same conditions (i.e. flux density), 10.3% of NP-EGTA was photolyzed when saturating $Ca^{a+}$ (3.0 mM) was present (FIG. 2b). Thus, the quantum yield of photolysis of the NP-EGTA:$Ca^{2+}$ complex is 0.23. In $Ca^{2+}$-free conditions, HPLC analysis (data not shown) indicated that 8.91% of NP-EGTA was photolyzed, implying that the quantum yield of photolysis of cation-free chelator is 0.20, therefore the $Ca^{2+}$-free chelator is photolysed with approximately the same efficiency as the NP-EGTA:$Ca^{2+}$ complex. This is about six (6) times greater than nitr-5 or nitr-7 (2) and the same as that of DM-nitrophen (4).

Cation Binding and Release

The affinity of NP-EGTA for $Ca^{2+}$ was obtained by titration of the chelator with incremental additions of $Ca^{2+}$. $[Ca^{2+}]_{free}$ (and hence $[Ca^{2+}]_{bound}$) was measured using fluo-3, a $Ca^{2+}$-selective indicator, which shows a fluorescence emission increase when $Ca^{2+}$ binds (18). The increases in $Ca^{2+}$-indicator fluorescence are shown in FIG. 3(a). A Scatchard analysis (FIG. 3a inset) of these data indicates the $K_d$ of NP-EGTA for $Ca^{2+}$ is 80 nM. This is higher than the parent EGTA chelator (150 nM at pH 7.2), but is a slightly lower affinity than nitr-7 (54 nM, 2) and is considerably lower than the EDTA-derived molecule, DM-nitrophen (5 nM, 4). For any chelator:$Ca^{a+}$ complex to function effectively as a caged Ca, the pre-photolysis affinity should be high for two reasons. First, it is crucial that the resting or pre-photolysis $[Ca^{2+}]$ is very low, i.e. that it is non-activating or sub-threshold for the biological system being investigated. The $K_d^{Ca}$ and the total amounts of $Ca^{2+}$ and chelator determine $[Ca^{2+}]_{free}$. Secondly, the percentage of chelator loaded with $Ca^{2+}$ before photolysis is important as this is a factor which determines how much $Ca^{2+}$ is liberated upon photolysis, as $Ca^{2+}$ can only be photoreleased if it is complexed. Also, if the chelator is frilly loaded, then the photoreleased $Ca^{2+}$ will not be rebound by unphotolysed, unloaded chelator, i.e. step increases rather than pulses of $Ca^{2+}$ will be produced (see ref. 19, 20).

The $K_d$ of the photoproducts also influences the amount of $Ca^{2+}$ released upon photolysis. The very efficient release of $Ca^{2+}$ from NP-EGTA (and DM-nitrophen) is a result of the fact that the iminodiacetic acid photoproducts (Scheme 1) have $K_d$'s for $Ca^{2+}$ in the mM range. Thus, the change in affinity for $Ca^{2+}$ upon photolysis is about 12,500-fold (nitr-7 changes by 56-fold, 2). The Table compares the free $[Ca^{2+}]$ before and after 50% photolysis of four currently available photosensitive chelators (NP-EGTA, DM-nitrophen, nitr-5 and nitr-7) at three different $[Ca^{2+}]$. Thus, resting $[Ca^{2+}]$ in a frog skeletal muscle fibre (0.18–0.22 mM, 21) can be achieved with [chelator]:$[Ca^{2+}]$ of 2 mM:1.50 mM for NP-EGTA and nitr-7. When 50% photolysis is accomplished only 3 mM $Ca^{2+}$ is released by nitr-7, whereas 186 mM $Ca^{2+}$ is liberated using NP-EGTA. In order to have a prephotolysis $[Ca^{2+}]$ of 0.145 mM, using nitr-5 as the photosensitive buffer, only 1.0 mM $Ca^{2+}$ can be present (see Table), and upon 50% photolysis 0.80 mM $Ca^{2+}$ is released. To activate full contraction of a frog skeletal muscle fiber, $[Ca^{2+}]_{free}$ should rise to about 5 mM (22), however the total amount of $Ca^{2+}$ which must be released in order to attain this $[Ca^{2+}]$ is two orders of magnitude higher than this value, as the $Ca^{2+}$-buffering capacity of the muscle fiber is about 350 mM (23). Therefore, large changes in $K_d$ upon photolysis are necessary to evoke sufficient $Ca^{2+}$-release from a caged Ca to produce full tension in a skeletal muscle fiber.

Photolysis occurs in the compounds of the present invention with light having a wavelength in the range of 250–500 nanometers.

Figure 3B:
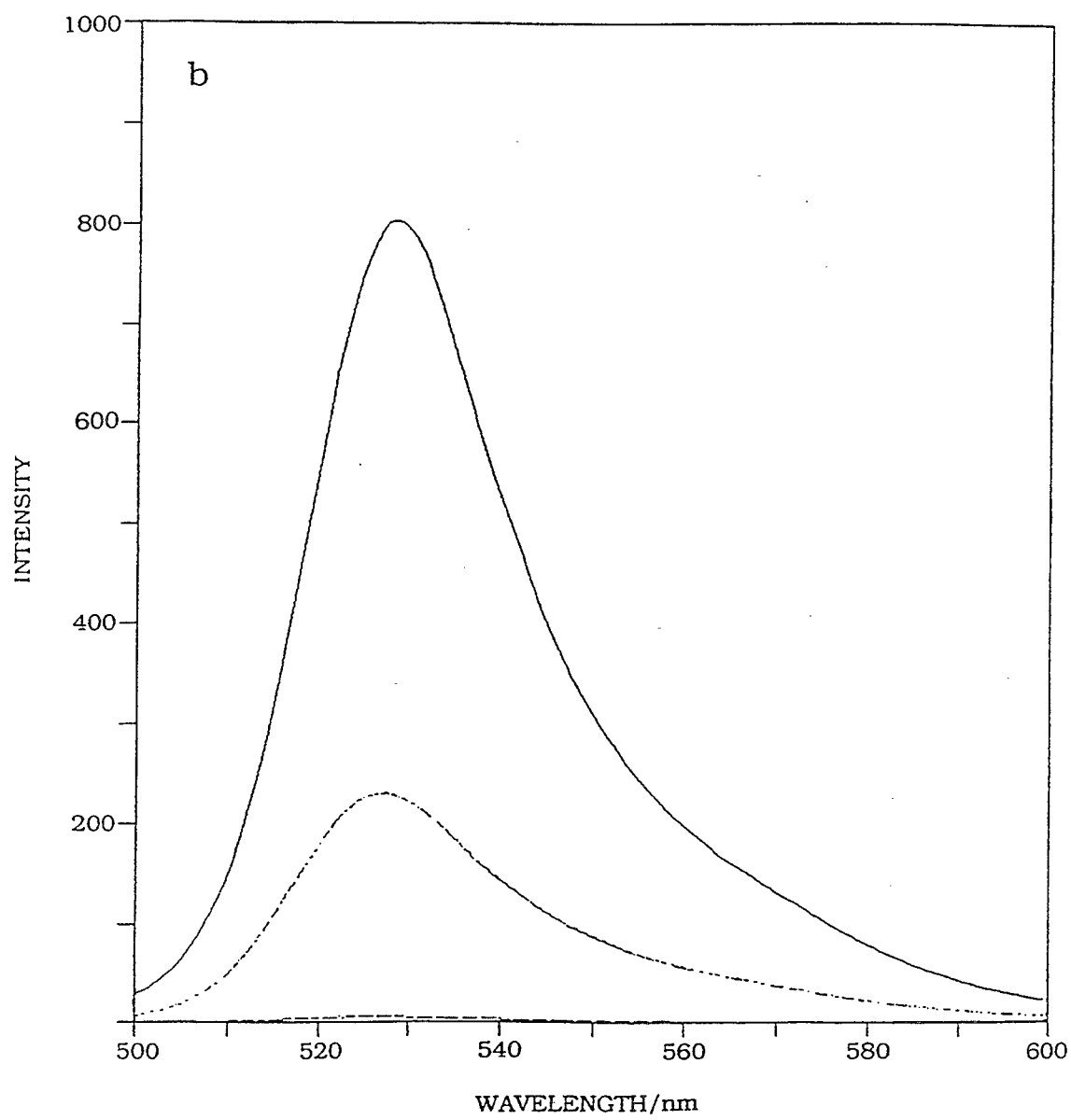
FIG. 3(b) shows the emission spectra of fluo-3, initial conditions as in (a), with [$Ca^{2+}$]=0.0; 0.55 mM or 0.55 mM & 1.0 mM $Mg^{2+}$ ($Mg^{2+}$ had no effect on the fluo-3 signal); 0.55 mM & 1.0 mM $Mg^{2+}$ with irradiation.
Figure 3E:
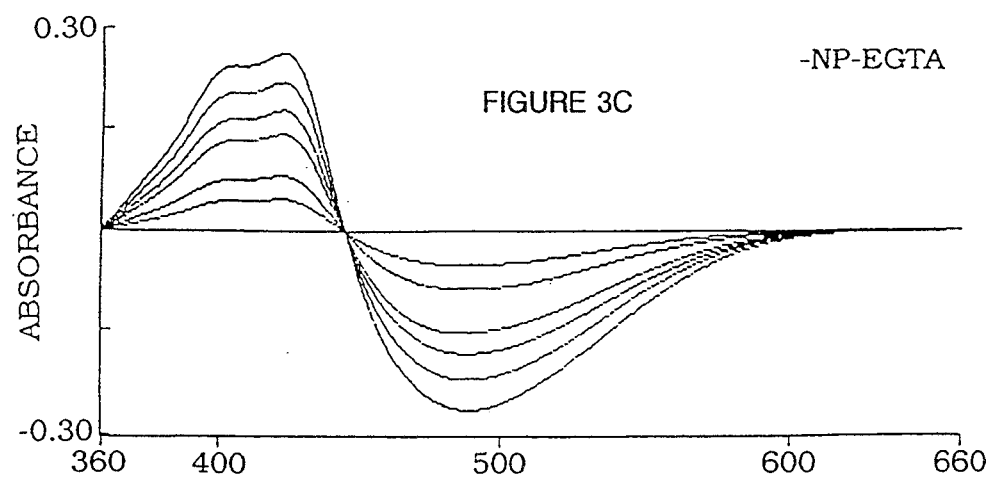
FIG. 3 shows the nitrophenyl-EGTA divalent cation affinities.
FIG. 3(a) shows the emission spectra of fluo-3 (excitation at 490 nm) resulting from titration of NP-EGTA (0.665 mM in 40 mM hepes, 100 mM KCl, pH 7.2, 20° C.) with 0.10 mM incremental additions of $Ca^{2+}$. Scatchard analysis of these data is inset.
FIG. 3(c) shows the absorption spectra of mag-fura-red (20 $\mu$M) in the same buffer without (top) and with, FIG. 3D, (middle) NP-EGTA (10mM) with incremental additions of $Mg^{2+}$. The bottom panel (FIG. 3E) shows a plot of $OD_{480}$ versus [$Mg^{2+}$] without (circles) and with (crosses) NP-EGTA.
Figure 3E:
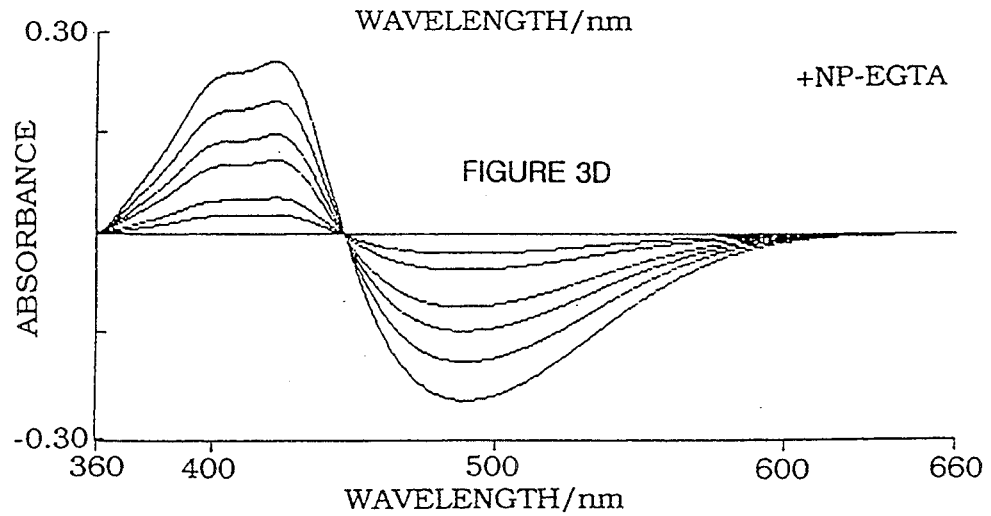
Figure 3E:
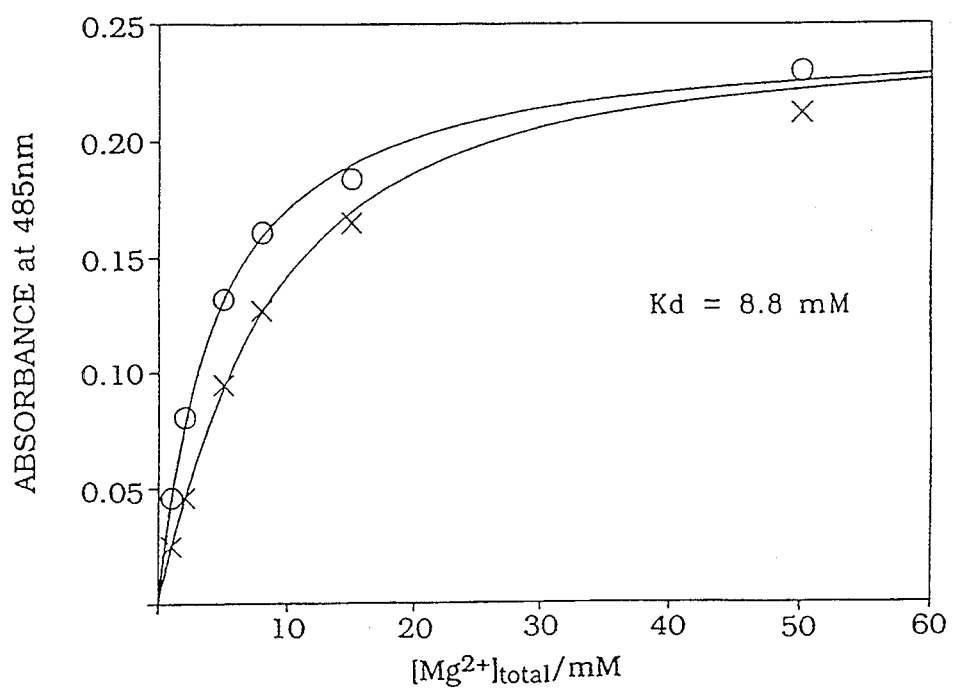

A clear advantage of the nitr series of photosensitive chelators compared to DM-nitrophen is their high selectivity for $Ca^{2+}$ over $Mg^{2+}$ (e.g. nitr-7 has $K_d^{Mg}=5.4$ mM). NP-EGTA possesses similar discrimination properties. The selectivity of NP-EGTA for $Ca^{2+}$ versus $Mg^{2+}$ is demonstrated by the lack of effect of the addition of 1 mM $Mg^{2+}$ to a 0.655 mM NP-EGTA solution which already contained 0.55 mM $Ca^{2+}$ (see FIG. 3b). There is no increase in the fluo-3 signal, indicating that NP-EGTA does not bind $Mg^{2+}$ significantly in the mM concentration range. Irradiation of this sample using a frequency-doubled ruby laser (347 nm emission) liberates $Ca^{2+}$ from the NP-EGTA:$Ca^{2+}$ complex as shown by the increase in the fluo-3 signal (FIG. 3b).

The $Mg^{2+}$ affinity of NP-EGTA was determined by titration of the $Mg^{2+}$-indicator, mag-fura-red (20 μM) without and with NP-EGTA (10 mM) in buffer (40 mM hepes, 100 mM KCl, pH=7.2) at 25° C. FIG. 3(c) shows the difference absorption spectra upon addition of 1, 2, 5, 8, 15, and 50 mM $Mg^{2+}_{total}$ to such a solution. The top panel shows the mag-fura-red spectra without NP-EGTA and the center panel with NP-EGTA. The bottom panel shows curves fitted to the absorbance at 480 nm for these two titrations (circles without NP-EGTA, crosses with NP-EGTA) using laws of mass action. The $K_d$ for $Mg^{2+}$ of NP-EGTA was determined to be 8.8 mM from these data.

Thus, at intracellular $[Ca^{2+}]$ and $[Mg^{2+}]$ only $Ca^{2+}$ is bound to the chelator and liberated upon photolysis.

Rapid $Ca^{2+}$ Release in Rabbit Skeletal Muscle Fiber

Figure 4:
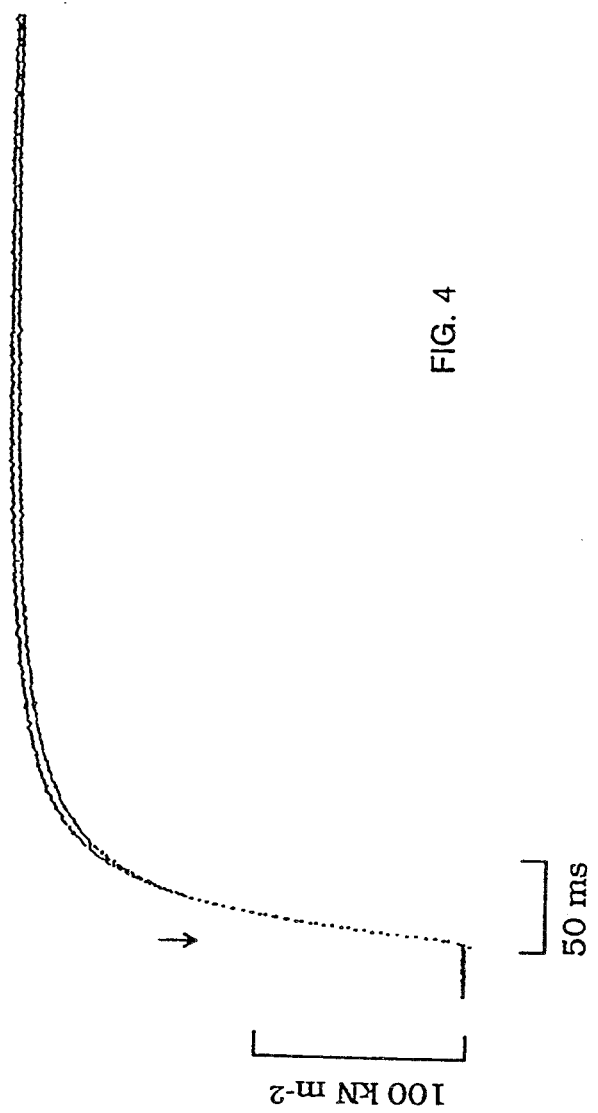
FIG. 4 shows the Ca-induced contraction of skinned skeletal muscle fibers. The arrow indicates the time of a pulse from a frequency-doubled ruby laser (347 nm). For DM-nitrophen, before photolysis, the muscle-bathing solution contained (mM): Tes (100), HDTA (27.91), ATP$Na_2$ (3.0), creatine phosphate (20), glutathione (10), DM-nitrophen (2.0), $MgCl_2$ (1.19), $CaCl_2$ (1.60). In the NP-EGTA solution there was (mM): Tes (100), HDTA (25.35), ATP$Na_2$ (5.50), creatine phosphate (20), glutathione (10), NP-EGTA (2.1), $MgCl_2$ (7.0), $CaCl_2$ (1.9). The pH of both solutions was 7.0; the ionic strength was 0.2M. Tension development was measured as in Ref. 24.

Photolysis of nitrophenyl-EGTA:$Ca^{2+}$ and DM-nitrophen:$Ca^{2+}$ complexes were used to release $Ca^{2+}$ rapidly in chemically skinned psoas fibers from rabbit skeletal muscle. Rapid development of maximal tension was elicited under two conditions: (1) [NP-EGTA:-$Ca^{2+}$]=1.9 mM, [ATP:$Mg^{2+}$]=5 mM and $[Mg^{2+}]_{free}=1$ mM; and (2) [DM-nitrophen:$Ca^{2+}$]=1.4 mM, [ATP:$Mg^{2+}$]=0.62 mM and $[Mg^{2+}]_{free}=40$ μM (see FIG. 4). The time to achieve half-maximal tension using NP-EGTA was 17.9 ms and 18.1 ms with DM-nitrophen at 15° C. (see FIG. 4). We have previously shown that $Ca^{2+}$-release from the DM-nitrophen:$Ca^{2+}$ complex is very rapid ($t_{\frac{1}{2}} \leq 180$ microseconds, 19) and, therefore, the photorelease process is not rate-limiting for contraction in skeletal muscle fibers. The fact that photorelease $Ca^{2+}$ from NP-EGTA:$Ca^{2+}$ and DM-nitrophen:$Ca^{2+}$ elicit identical, rapid tension transients in skeletal muscle indicates that release of $Ca^{2+}$ from NP-EGTA is also not rate-limiting. Furthermore, under the conditions of photolysis (100 mJ pulse from a frequency-doubled ruby laser), the NP-EGTA:$Ca^{2+}$ complex releases sufficient $Ca^{2+}$ to generate full tension in the muscle fiber. It is interesting that there are no major effects, on the rate of the development of tension nor on the maximal contraction, due to a change in $[Mg]_{free}$ from 40 μM to 1 mM in these experiments.

We have developed and characterized a new $Ca^{2+}$-specific chelator, which has high affinity for $Ca^{2+}$ and which upon photolysis rapidly releases the complexed $Ca^{2+}$ with good quantum efficiency. We anticipate that nitrophenyl-EGTA will be useful for studying intracellular processes involving changes in $[Ca^{2+}]$. Furthermore, in conjunction with DM-nitrophen, systematic studies on the role of $Mg^2+$ in these processes can also be undertaken.

In addition, the ring structure of the nitrophenyl-EGTA compound of the present invention may also be substituted as disclosed in our U.S. Pat. No. 4,981,985, and shown in Scheme 3, wherein the substituents of $R_1$ to $R_4$ are each chosen from the group consisting of hydrogen, methoxy, halogen, methyl, hydroxy, vinyl, nitro, dimethylamine, and thioalkyl and wherein $R_5$ and $R_6$ are each chosen from the group consisting of hydrogen, methyl or ethyl.

The present invention also includes various substituted intermediate structures, such as the intermediate structure (4) of Scheme 2: o-Nitrophenyl-bromoacetaldehyde Bis-2-(2-chloroethoxy)-ethyl Acetal, wherein $R_1$ to $R_4$ are each chosen from the group consisting of hydrogen, methoxy, halogen, methyl, hydroxy, vinyl, nitro, dimethylamine and thioalkyl.

The present invention includes the substituted intermediate structure (5) shown in Scheme 2: 2-(2-chloroethoxy)-ethyl 2-o-Nitrophenyl-2-bromoethyl Ether, wherein $R_1$ to $R_4$ are each chosen from the group consisting of hydrogen, methoxy, halogen, methyl, hydroxy, vinyl, nitro, dimethylamine and thioalkyl.

The present invention also includes the substituted intermediate structure (6): 2-(2-azaethoxy)-ethyl 2-o-Nitrophenyl-2-azaethyl Ether, wherein $R_1$ to $R_4$ are each chosen from the group consisting of hydrogen, methoxy, halogen, methyl, hydroxy, vinyl, nitro, dimethylamine and thioalkyl.

Without further elaboration the foregoing will so fully illustrate our invention that others may, by applying current or future knowledge, adapt the same for use under various conditions of service.

REFERENCES (1) Kaplan, J. H. (1990) *Annu. Rev. Physiol.* 52, 897–914.
(2) Adams, S. R., Kao, J. P. Y., Grynkiewicz, G., Minta, A., & Tsien, R. Y. (1988) *J. Am. Chem. Soc.* 110, 3212–3220.
(3) Ellis-Davies, G. C. R., & Kaplan, J. H. (1988) *J. Org. Chem.* 53, 1966–1969.
(4) Kaplan, J. H., & Ellis-Davies, G. C. R. (1988) *Proc. Natl. Acad. Sci. U.S.A.* 55, 6571–6575.
(5) Morad, M., Davies, N. W., Kaplan, J. H., & Lux, H. D. (1988) *Science* 241, 842–844.
(6) Niggli, E. and Lipp, P. (1993) *Biophys J.* 55 400a.
(7) Naebauer, M., Ellis-Davies, G. C. R., Kaplan, J. H. & Morad, M. (1989) *Am. J. Physiol.* 256, H916-20.
(8) Delaney, K. R., & Zucker, R. S. (1990) *J. Physiol.* 426, 473–498.
(9) Rapp, G., Poole, K. J. V., Maeda, Y., Kaplan, J. H., Ellis-Davies, G. C. R., McCray, J. A., & Goody, R. S. (1990) *Bunsenges. Phys. Chem.* 93, 410–424.
(10) Iino, M, & Endo, M (1992) *Nature* 360, 76–78.
(11) Allen, T. S., Barsoff, R. J., Ellis-Davies, G. C. R., Kaplan, J. H. Goldman, Y. E., Martyn, D. A., & Gordon, A. M. (1993) *Biophys. J.* 64, 135a.
(12) Neher, E. & Zucker, R. S. (1993) *Neuron* 10, 21–30.
(13) Thomas, P., Wong, J. G., & Almers, W., (1993) *EMBO J.* 12, 303–306.
(14) Johnson, B. D. & Byerly, L. (1993) *J. Physiol.* 462, 321–347.
(15) Backx, P. H., O'Pouke, B., & Marban, E. (1991) *Am. J. Hypertens.* 4, 416S–421S.
(16) Zucker, R. S. (1992) *Cell Calcium* 13, 29–40.
(17) Kaplan, J. H., Forbush, B., & Hoffman, J. F. (1978) *Biochemistry* 17, 1929–1935.
(18) Minta, A., Kao, J. P. Y., & Tsien, R. Y. (1989) *J. Biol. Chem.* 264, 8171–8178.
(19) McCray, J. A., Fidler-Lim, N., Ellis-Davies, G. C. R., & Kaplan, J. H. (1992) *Biochemistry* 31, 8856–8861.
(20) Zucker, R. S. (1993) *Cell Calcium* 14, 87–100.
(21) Harkins, A. B., Kurebayashi, N., & Baylor, S. M. (1993) *Biophys. J.* 64, 241a
(22) Konishi, M. & Baylor, S. M. (1991) *J. Gert Physiol.* 97, 245–270.
(23) Pape, P. C., Konishi, M., Hollingworth, S., & Baylor, S. M. (1990) *J. Gen. Phys.* 96, 493–516.
(24) Goldman, Y. G., Hibberd, M. G., & Trentha, D. R. (1984) *J. Physiol.* 354, 701–705.
(25) Ellis-Davies, G. C. R., Kaplan, J. H., U.S. Pat. No. 4,981,985.

We claim:
1. A compound of the formula:

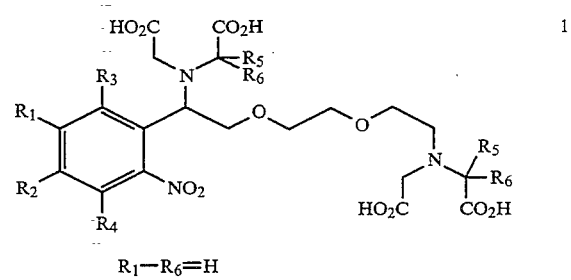

$R_1$—$R_6$=H ortho-nitrophenyl-ethylenebis ( oxyethylenenitrilo )tetraacetic acid.

2. A solution comprising a photolabile chelator consisting essentially of an anion having the following structure:

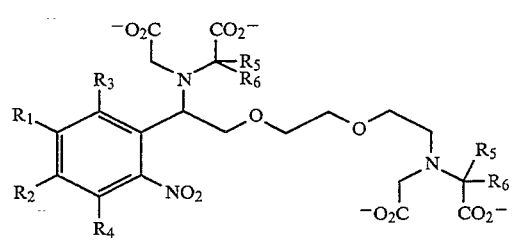

wherein $R_1$, $R_2$, $R_3$, $R_4$, $R_5$ and $R_6$ are chosen from the group consisting of hydrogen, methoxy, halogen, methyl, hydroxy, vinyl, nitro, amino, dimethylamine and thioalkyl.

3. A compound consisting of the photolabile chelator anion having the structure shown in claim 2 chelated with a multivalent cation.

4. The chelated compound of claim 3 wherein the multivalent cation is chosen from the group consisting of calcium, zinc, cadmium, manganese and iron.

5. The chelated compound of claim 3 wherein light in the range of 250–500 nanometers causes the photolabile chelator to split and form compounds having the following two structures:

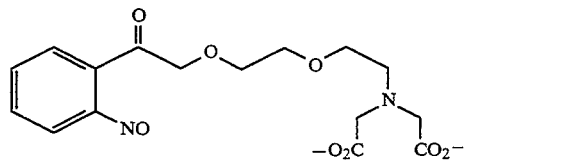

6. A method of synthesizing orthonitrophenyl-ethylenebis(oxyehtylenenitrilo)tetraacetic acid in accordance with the following steps:

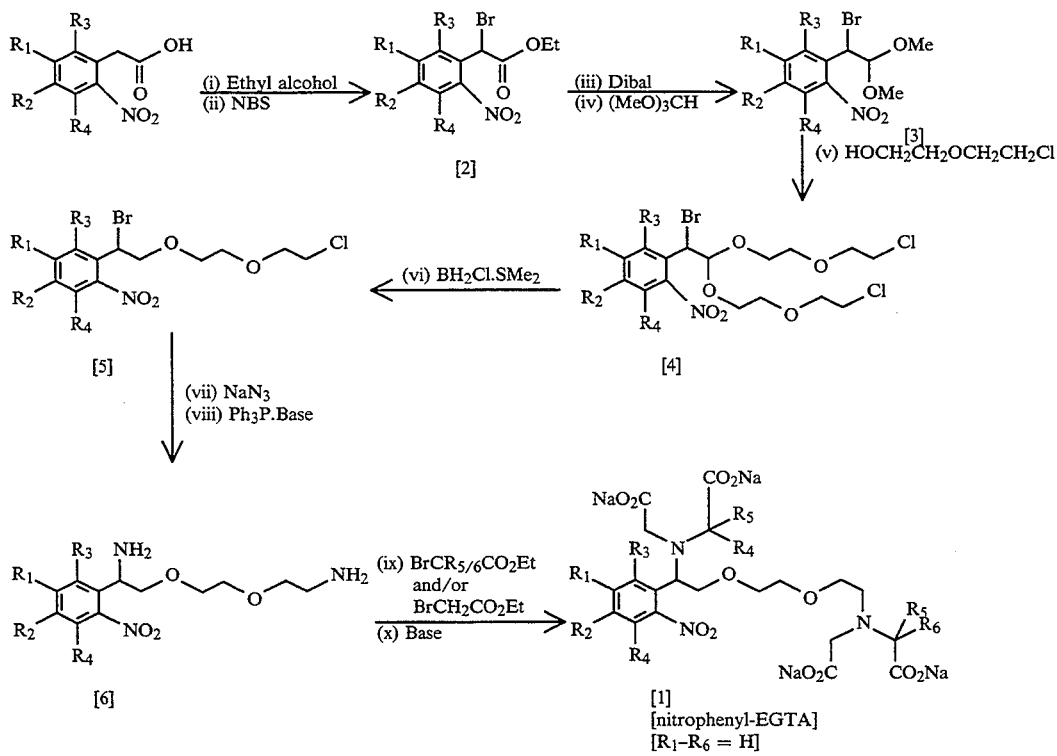

wherein $R_1$ to $R_4$ are each chosen from the group consisting hydrogen, methoxy, halogen, vinyl, nitro, dimethylamine and thioalkyl; $R_5$ and $R_6$ are hydrogen.

7. A method of producing a high photochemical yield of liberated calcium comprising the steps of:
(a) binding calcium ions with 4-(2'-nitrophenyl)-3,13-bis[carboxymethyl]-6,9-dioxa-3,12-diazatet-radecanedioic acid; and
(b) subjecting the product of step (a) to photolysis.

8. The method of claim 7 wherein the photolysis utilizes fight having a wavelength in the range of 250–500 nanometers.

9. A compound of the following structure:

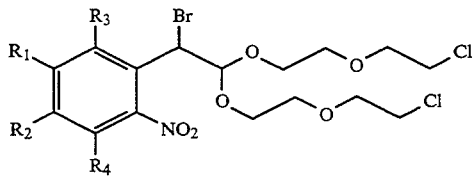

wherein $R_1$ to $R_4$ are each chosen from the group consisting of hydrogen, methoxy, halogen, methyl, hydroxy, vinyl, nitro, dimethylamine and thioalkyl.

10. A compound of the following structure:

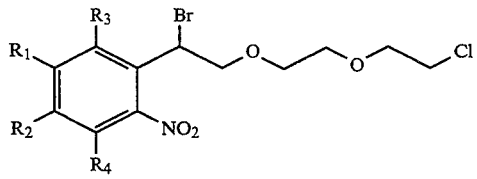

wherein $R_1$ to $R_4$ are each chosen from the group consisting of hydrogen, methoxy, halogen, methyl, hydroxy, nitro, dimethylamine and thioalkyl.

11. A compound of the following structure:

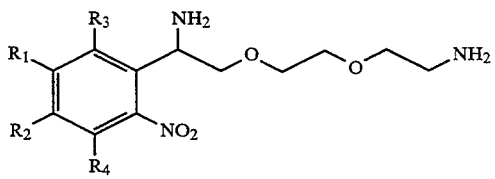

wherein $R_1$ to $R_4$ are each chosen from the group consisting of hydrogen, methoxy, halogen, methyl, hydroxy, vinyl, nitro, dimethylamine and thioalkyl.

* * * * *